United States Patent
Karmazyn et al.

(10) Patent No.: US 9,492,136 B2
(45) Date of Patent: Nov. 15, 2016

(54) METHOD AND APPARATUS THAT AUTOMATES TUBE CURRENT AND VOLTAGE SELECTION FOR CT SCANS

(71) Applicant: Indiana University Research & Technology Corporation, Indianapolis, IN (US)

(72) Inventors: Boaz Karmazyn, Indianapolis, IN (US); Yun Liang, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 296 days.

(21) Appl. No.: 14/370,517

(22) PCT Filed: Jan. 4, 2013

(86) PCT No.: PCT/US2013/020250
§ 371 (c)(1),
(2) Date: Jul. 3, 2014

(87) PCT Pub. No.: WO2013/103790
PCT Pub. Date: Jul. 11, 2013

(65) Prior Publication Data
US 2014/0376688 A1  Dec. 25, 2014

Related U.S. Application Data

(60) Provisional application No. 61/583,873, filed on Jan. 6, 2012, provisional application No. 61/583,700, filed on Jan. 6, 2012.

(51) Int. Cl.
*A61B 6/00* (2006.01)
*A61B 6/03* (2006.01)

(52) U.S. Cl.
CPC .................. *A61B 6/544* (2013.01); *A61B 6/03* (2013.01); *A61B 6/032* (2013.01); *A61B 6/40* (2013.01);

(Continued)

(58) Field of Classification Search
CPC ........ A61B 6/032; A61B 6/542; A61B 6/06; A61B 6/405; A61B 6/544
See application file for complete search history.

(56) References Cited

U.S. PATENT DOCUMENTS 6,775,352 B2    8/2004    Toth et al.
7,106,824 B2    9/2006    Kazama et al.
(Continued)

FOREIGN PATENT DOCUMENTS

JP    2008-220452 A    9/2008
KR    10-2007-0103862 A    10/2007

OTHER PUBLICATIONS

Jan Menke, Md; Comparison of Different Body Size Parameters for Individual Dose Adaptation in Body CT of Adults; Radiology; Aug. 2005; pp. 565-571.
(Continued)

*Primary Examiner* — Hoon Song
(74) *Attorney, Agent, or Firm* — Faegre Baker Daniels LLP

(57) ABSTRACT

A CT scanner and method of operating the CT scanner enables customized automated selection of tube current and peak tube voltage for a CT scan. The CT scanner receives data, each datum of which corresponds to a reference image quality (noise level at a certain tube voltage) for patient water equivalent diameter ("WED") body size. The CT scanner then stores the noise level and patient WED, and a processor in the CT scanner generates a curve corresponding to acceptable noise levels as a function of water equivalent diameter. The CT scanner stores the curve in a memory associated with the scanner and the CT scanner is subsequently operated with reference to the curve stored in the memory. The tube voltage that can generate the reference CT scan quality (signal-to-noise ratio) with the lowest radiation dose to the patient is selected.

6 Claims, 4 Drawing Sheets

(52) U.S. Cl.
CPC ............. *A61B 6/488* (2013.01); *A61B 6/5258* (2013.01); *A61B 6/5294* (2013.01); *A61B 6/542* (2013.01); *A61B 6/545* (2013.01); *A61B 6/58* (2013.01); *A61B 6/583* (2013.01)

(56) References Cited

U.S. PATENT DOCUMENTS

| | | |
|---|---|---|
| 7,813,473 B2 | 10/2010 | Edic et al. |
| 8,155,263 B2 | 4/2012 | Wu et al. |
| 2009/0141854 A1 | 6/2009 | Hirokawa et al. |
| 2010/0322375 A1 | 12/2010 | Hirokawa et al. |
| 2012/0014499 A1 | 1/2012 | Feuerlein et al. |
| 2014/0270053 A1* | 9/2014 | Larson .................. A61B 6/032 378/4 |

OTHER PUBLICATIONS

Written Opinion of the International Searching Authority corresponding to PCT Application No. PCT/US2013/020250; Korean Intellectual Property Office, Metropolitan City, Republic of Korea; Apr. 29, 2013; 6 pages.
Fletcher, MD, J. G.; Adjusting kV to Reduce Dose or Improve Image Quality—How to Do it Right; Technology Assessment Institute: Summit on CT Dose; 62 Pages; Mayo CT Clinic Innovation Center and Department of Radiology, http://mayoresearch.mayo.edu/CTCIC.

* cited by examiner

METHOD AND APPARATUS THAT AUTOMATES TUBE CURRENT AND VOLTAGE SELECTION FOR CT SCANS

CLAIM OF PRIORITY

This application claims priority from U.S. Provisional Application No. 61/583,700, which is entitled "CUSTOMIZED AUTOMATED TUBE CURRENT AND VOLTAGE SELECTION IN CT SCANS," and was filed on Jan. 6, 2012.

This application further claims priority from U.S. Provisional Application No. 61/583,873, which is entitled "CUSTOMIZED AUTOMATIC TUBE CURRENT AND VOLTAGE SELECTION IN CT SCANS," and was filed on Jan. 6, 2012. This application further claims priority from PCT Application No. PCT/US2013/020250, which is entitled "METHOD AND APPARATUS THAT AUTOMATES TUBE CURRENT AND VOLTAGE SELECTION FOR CT SCANS," and was filed on Jan. 4, 2013.

TECHNICAL FIELD

The present disclosure relates generally to X-ray imaging and, more specifically, to systems and methods of computed tomography (CT).

BACKGROUND

X-ray scans and X-ray computed tomography (CT) scans are used in a wide range of medical and industrial settings to generate images of structures within a three-dimensional subject that are otherwise invisible to the naked eye. For example, CT scans of medical patients are used in a wide range of pathologies including, but not limited to, identification of tumors, infectious process, infarctions, calcification, hemorrhage, and trauma.

While X-ray and CT scans are widely used, the X-ray radiation that is generated during the scans may increase risk of cancer for the patient being scanned. One goal is to control the exposure to radiation for humans and other living subjects that undergo the CT scan while also generating images with sufficient clarity and resolution to be useful in diagnostic procedures. This balance between the need to use the lowest X-ray radiation while maintaining an image quality required for optimal identification of pathology is known as ALARA "as low as reasonably achievable." During a CT scan, an X-ray source, such as an X-ray emitting tube, rotates around the longitudinal axis of the patient while emitting X-ray radiation. Some of the X-ray energy passes through the patient to a detector on the opposite side of the patient from the X-ray emitter, while the patient absorbs a portion of the X-ray energy. Certain structures in the patient, such as bones, fat, muscles, and water, absorb different amounts of energy resulting in different amounts of X-ray energy passing to the detectors. The information on the absorbed dose by the detectors at each position of the X-ray tube around the body is transferred to image processing systems that are known to the art that generate two and three dimensional models of structures in the patient using the individual X-ray images.

During a CT scan, a subject is typically positioned on a movable member such as a sliding table. The sliding table moves through an annular opening that is surrounded by the series of X-ray detectors. The X-ray source revolves around the patient as the patient moves through the annular opening on the sliding table to generate a series of X-ray images. The patient absorbs a portion of the X-rays, while other X-rays pass through the patient and reach the detectors during the imaging process. There is a tradeoff between the quality of images and the amount of X-ray energy that the patient absorbs. For example, a lower energy X-ray scan produces images that have high noise level and/or poor contrast, which can obscure details about structures within the patient. Increasing the intensity of the X-ray exposure improves the quality of images, but the patient also absorbs additional X-ray radiation during the scan.

The amount of X-ray radiation delivered to the patient and the quality of the image are dependent on the tube current (mAs) and the peak tube voltage (kVp). The power output of the tube is expressed as a product of the tube current and peak tube voltage. The dosage that the patient receives from the CT scanner corresponds to the portion of the emitted power from the tube that is absorbed by the tissue in the body of the patient multiplied by the length of time that the patient is exposed to the X-rays from the tube. For example, a higher level of tube current and higher peak tube voltage generally results in a higher quality image, but delivers X-ray radiation to the patient at a correspondingly higher rate. Existing CT systems generally have several options for constant tube voltage, which typically include 140 kVp, 120 kVp, 100 kVp and 80 kVp. In these systems, the tube voltage and current are selected based on the patient's weight, the type of scan, and the radiologist's preference of image quality.

These competing constraints present challenges for operating a CT system. The human body size ranges from a size of a baby to an obese adult. Different tube voltages and tube currents are needed to optimize the study for each body size. In addition, the image quality and tolerance to image noise are different for various body sizes. Many current systems use body weight to guide tube voltage and current settings. One drawback to selecting tube current and voltage based on the patient's weight is that weight alone is not necessarily a good representation of the quantity of X-ray energy a subject will absorb. For example, a subject who is at a particular weight, but is shorter and overweight, will typically absorb more X-ray energy than a subject who is at that same weight, but is taller and not overweight. One other challenge is that every group of radiologists may have different preferences of image quality based on experience, patient population and prevalence of specific pathologies.

Automating the current and voltage selection process reduces some of the variability in image quality between CT scans performed in patients with different body size and habitus. These methods are based on the water equivalent diameter (WED) of the scanned area of the patient's body as calculated from the scout view. Typically, one or few algorithms determine the change in the tube current based on the scanned WED and a preference of image quality. However, the preference of image quality is different for every body size. In a smaller body size, less image noise is typically preferred. Institutions typically have patients with differing demographics and many institutions specialize in particular types of services and diseases with a specific preference to CT scan image quality. A graph comparing the image quality preferences of two different institutions for different WEDs is shown in FIG. 4. Consequently, an automated procedure with a predetermined algorithm of change in tube current and voltage with change in scanned WED may be insufficient to meet the needs of a variety of institutions. The process of optimizing CT scans with the currently known processes may require many trial and error CT scans Improved automation of tube current and peak voltage selection that is based on the specific customer preferences of image quality is therefore desirable.

SUMMARY

In one embodiment a method of operating a CT scanner enables customized automated selection of tube current and peak tube voltage for a CT scan. The method includes receiving with a processor data associated with the CT scanner. Each datum of the data received includes a noise level and a water equivalent diameter for a patient imaged in a CT scan that has an image quality above a predetermined image quality threshold. The method further comprises storing the data in a memory associated with the CT scanner, generating with the processor associated with the CT scanner a curve identifying acceptable noise levels with reference to the water equivalent diameters in the data, storing the curve in the memory, and operating the CT scanner to perform a subject scan with reference to the curve stored in the memory and a water equivalent diameter for a patient to be imaged.

In another embodiment, a CT scanner enables customized automated selection of tube current and peak tube voltage for a CT scan. The CT scanner includes an x-ray source, a plurality of x-ray detectors, and a controller operatively connected to the x-ray source and the plurality of x-ray scanners. The controller is associated with a memory and is configured to receive data corresponding to images generated by the plurality of x-ray scanners. Each datum of the data includes a noise level and a water equivalent diameter for a patient imaged in a CT scan having an image quality above a predetermined image quality threshold. The controller is further configured to store the data in the memory, generate a curve identifying acceptable noise levels with reference to the water equivalent diameters in the data, store the curve in the memory, and operate the x-ray source to perform a subject scan with reference to the curve stored in the memory and a water equivalent diameter for a patient to be imaged.

DETAILED DESCRIPTION

As used herein, the term "water equivalent diameter" ("WED") represents the diameter of a cylinder of water, or water phantom, that attenuates an equal amount of X-ray energy as an area scanned in a patient. The water equivalent diameter is a function of the patient's size, body composition, geometry, density, and organs of body parts scanned.

Figure 1:
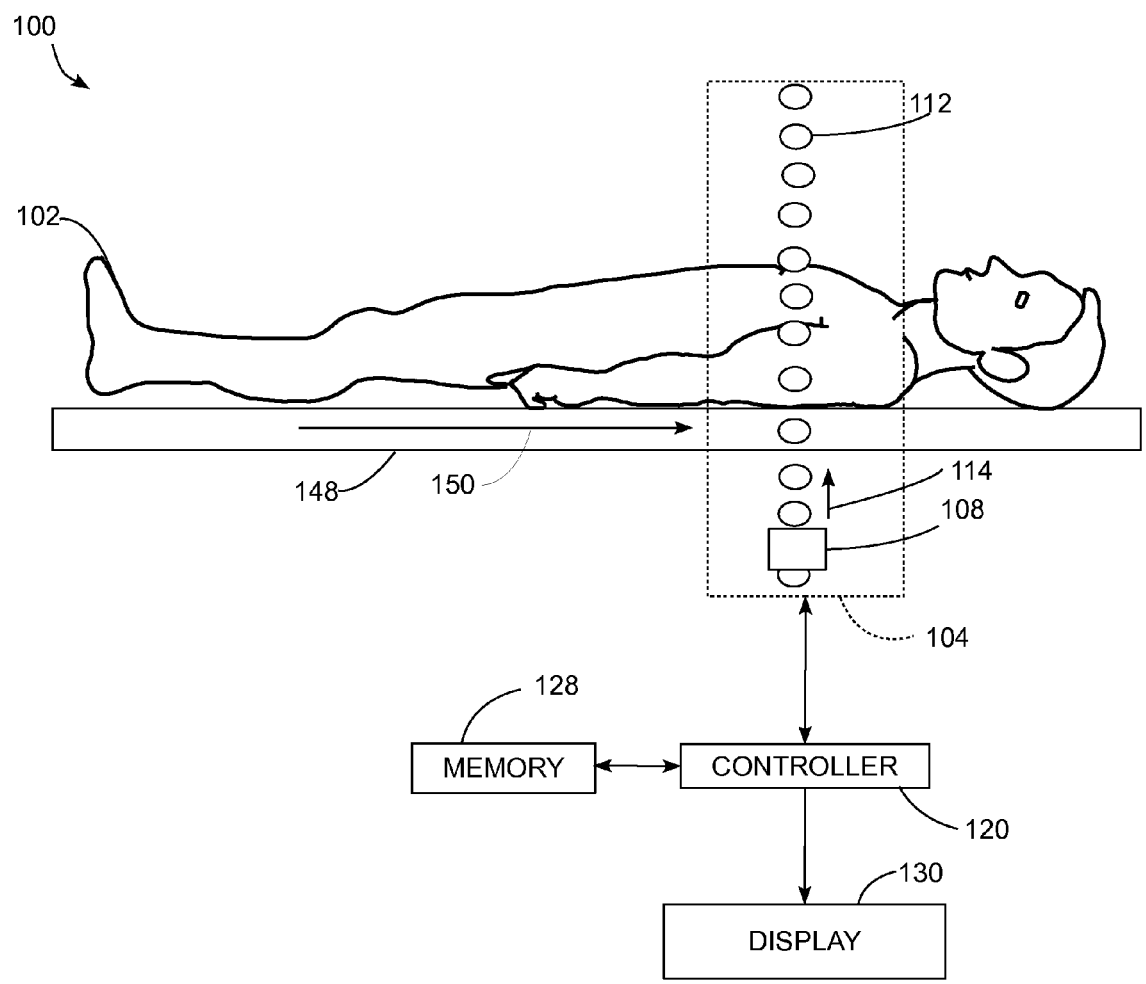
FIG. 1 is a schematic diagram of a CT scanner.

FIG. 1 depicts an exemplary CT scanner 100 that is configured to scan a human patient 102. The CT scanner 100 includes a scanner assembly 104, controller 120, memory 128, display device 130, and a sliding table 148. The scanner assembly 104 includes an X-ray source 108, such as an X-ray tube, and a plurality of X-ray detectors 112. As is known in the art, the scanner assembly 104 can be formed with an annular shape with the X-ray detectors 112 arranged in a circular configuration and a circular opening that enables the sliding table 148 and patient 102, moving in direction 150, to pass through the opening. The X-ray source 108 revolves around the patient 102 in direction 114, and the detectors 112 detect portions of the X-rays that pass through the patient 102 to generate a series of images, which are referred to as "slices." The controller 120 can store the image data in the memory 128 and display the image using the display device 130.

In the CT scanner 100, the controller 120 is operatively connected to the X-ray source 108, detectors 112, actuators for the slidable table 148, memory 128, and display 130. The controller 120 includes one or more digital logic devices such as microprocessors, microcontrollers, digital signal processors (DSPs), field programmable gate arrays (FPGAs), application specific integrated circuits (ASICs), and the like. The controller 120 executes stored programmed instructions that are stored in the memory 128. In the CT scanner 100, the controller 120 operates a motor or other actuator to control the revolution of the X-ray source 108. The controller 120 also controls the level of electrical current and the tube voltage used to generate X-rays with the X-ray source 108 and the tube voltage. The controller 120 synchronizes the operation of the X-ray source 108 with movement of the table 148 to apply a selected level of X-ray radiation to different segments of the patient 102.

The controller 120 generates two-dimensional images and three-dimensional models from a composition of multiple individual images that are generated by the scanner assembly 104. The display device 130, which typically includes one or more monitors, displays the images for analysis by a doctor or other healthcare professional. The controller 120 can also be configured to store the images in the memory 128 for future use, and in some embodiments the controller 120 can transmit the image data to a remote location using a data network such as a local area network (LAN) or wide area network (WAN).

Figure 2:
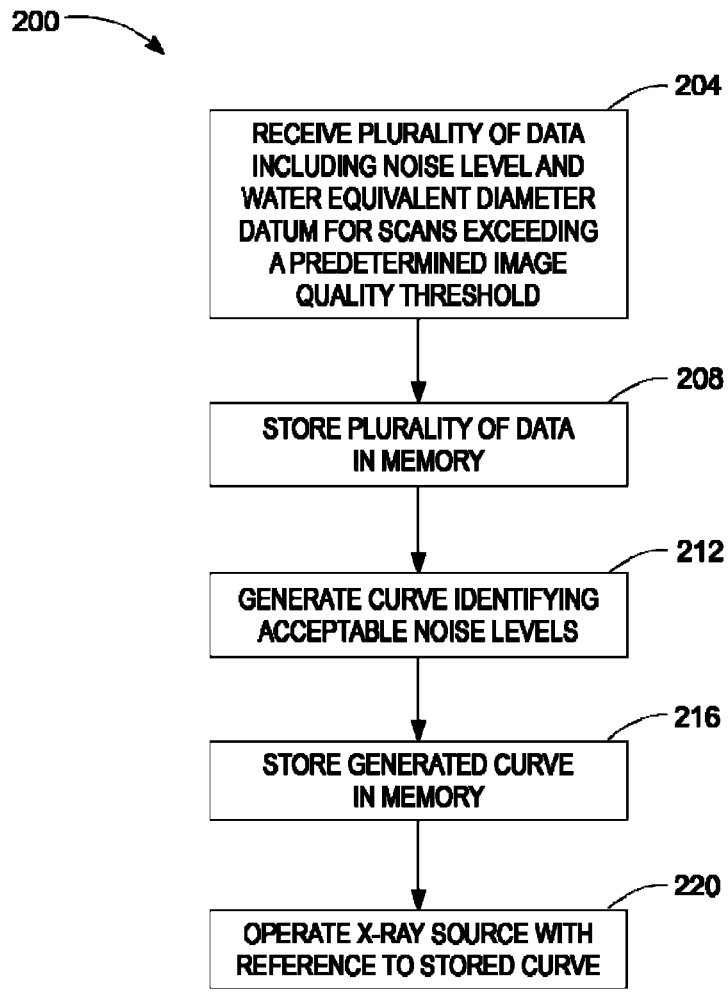
FIG. 2 is a block diagram of a process for customized automation of CT operation.

FIG. 2 depicts a process 200 for customized automatic operation of a CT scanner. In the discussion below, a reference to an action or function of a component in a CT scanner performed by the process 200 refers to execution of one or more programmed instructions that are performed by a control device, for example controller 120, to carry out the action or function in conjunction with components in the CT scanner. FIG. 2 is described with reference to FIG. 1 for illustrative purposes.

Process 200 begins with the controller 120 receiving data from past scans having an image quality that satisfies the preference of the users (block 204). Each datum in the data corresponds to a water equivalent diameter and a noise level from a past scan. The predetermined image quality can be a quantitative number based on an objective measure of image quality, or the predetermined threshold can be a subjective measure of image quality made by a radiologist or other professional evaluating the image. The data are received from a single institution or hospital, or a group of related institutions or hospitals. The data are, therefore, representative of the noise level requirements for the particular institution or group of related institutions. In some embodiments, the data can be unique to a particular department within a hospital or group of hospitals, or to a specific radiologist. The data typically include the noise level and WED used for a scan performed at a standard, or reference, peak tube voltage, which is typically 120 kVp.

The data are then stored in the memory 128 that is associated with the controller 120 (block 208). After the data are stored in the memory 128, the controller 120 generates a curve identifying acceptable noise levels with reference to patient water equivalent diameter for the reference voltage (block 212). The curve can be, for example, a best fit curve such as an exponential or polynomial fit curve. The curve, and, in some embodiments, an equation that is representative of the curve, is stored in the memory 128 of the CT scanner (block 216). It is known, for example, that a scan of a patient or an area of a patient having a higher water equivalent diameter enables a greater tolerance of noise in the resulting scan image. Therefore, as discussed in detail below, the controller 120 operates the X-ray source of the CT scanner with reference to the curve identifying the acceptable noise levels (block 220).

Figure 3:
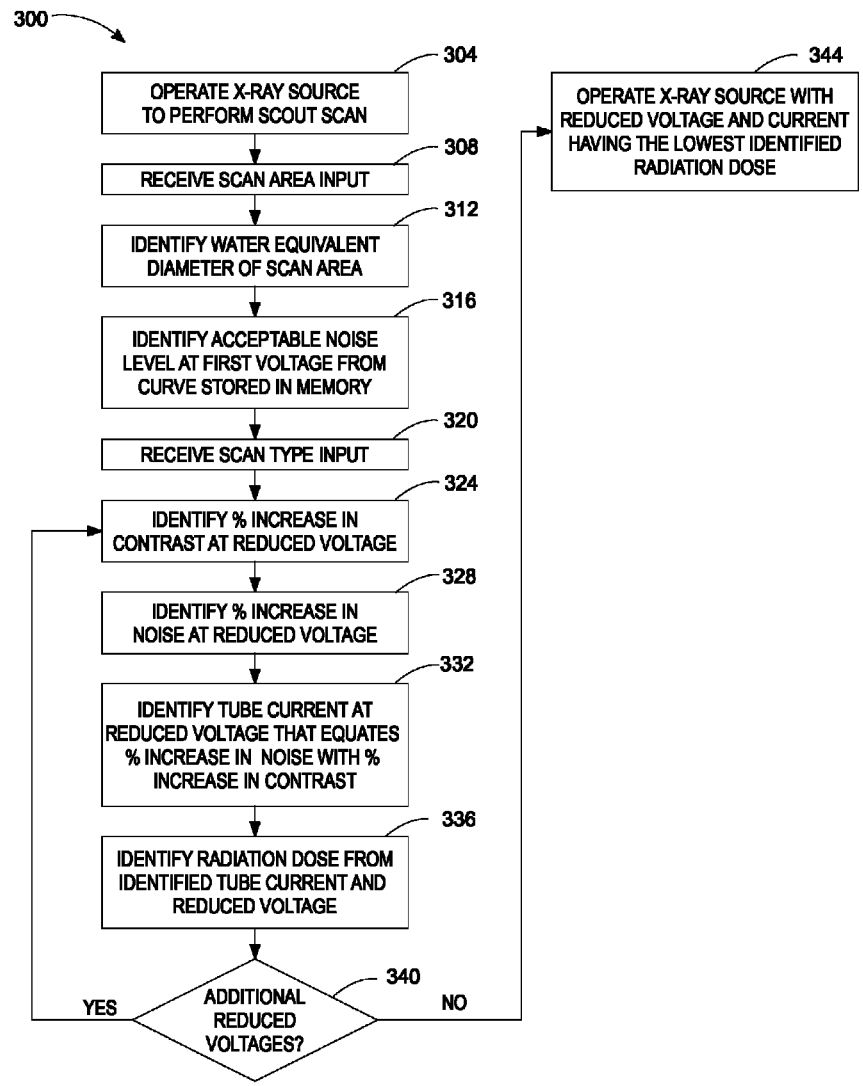
FIG. 3 is a block diagram of a process for selecting current and voltage for a CT scan.
Figure 4:
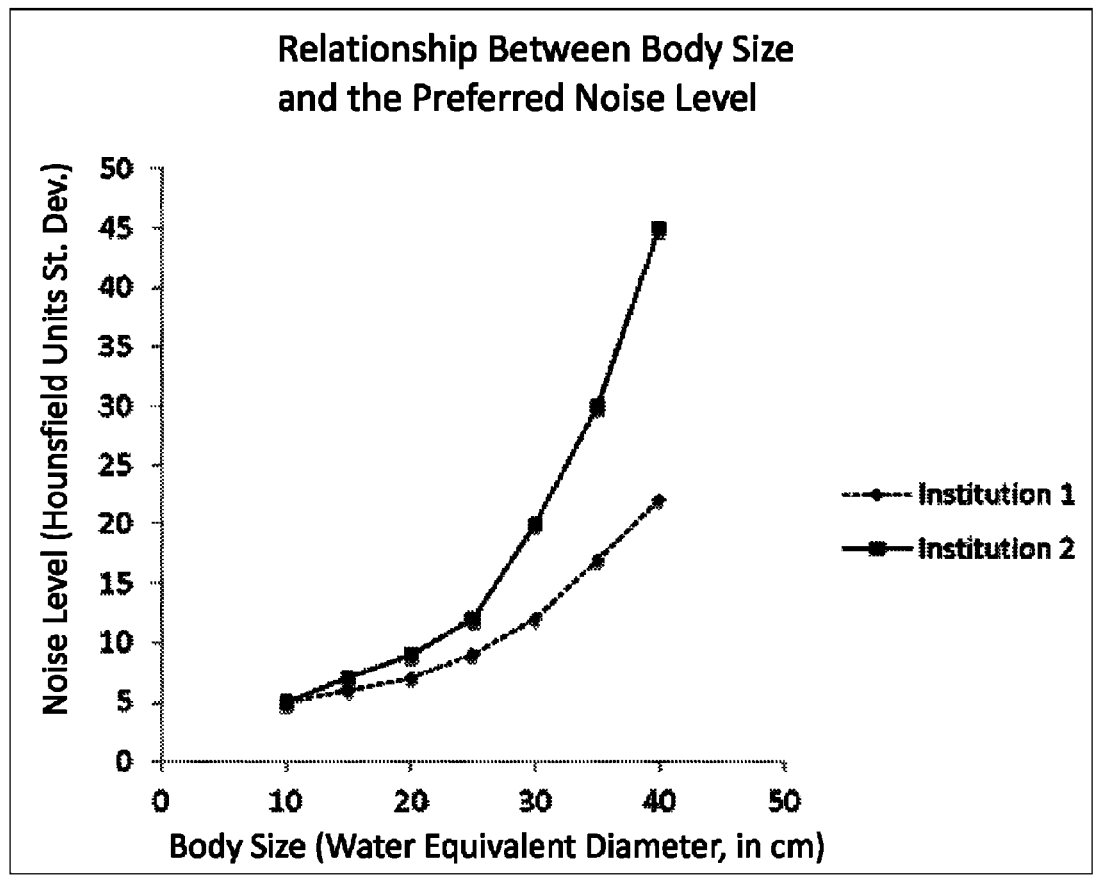
FIG. 4 is a graph demonstrating the relationship of body scanned WED to the noise preference in a tube voltage of 120 kVp at two different institutions.

FIG. 3 depicts a process 300 for customized automated selection of tube current and peak voltage for a CT scan. In the discussion below, a reference to an action or function of a component in a CT scanner performed by the process 300 refers to execution of one or more programmed instructions that are performed by a control device, for example controller 120, to carry out the action or function in conjunction with components in the CT scanner. FIG. 3 is described with reference to FIG. 1 for illustrative purposes.

The process 300 begins with the controller operating the X-ray source 108 to perform a scout scan of the patient (block 304). A scout scan is an initial scan performed at low power to generate low-resolution images of the patient. The controller 120 then receives a scan area, representing the area of the patient that will be scanned in detail (block 308). The scan area is typically input from an operator of the CT scanner. Using the scan area and the image data from the scout scan, the controller 120 calculates a water equivalent diameter of the scan area of the patient (block 312). The controller 120 then accesses the curve, discussed above with reference to FIG. 2, stored in memory 128 to determine the customized acceptable noise level at a first tube peak voltage, which is typically 120 kVp, for the identified WED of the patient and scan area (block 316). Next, the controller 120 receives a scan type, which is generally input to the CT scanner by an operator (block 320). The scan type can be, for example, an angiography CT scan, a routine intravenous contrast CT scan, a non-contrast CT scan, or any other type of CT scan.

Based on the type of the CT scan, the controller identifies a percent change in the contrast of the image by reducing the peak voltage from the first voltage, 120 kVp, to a reduced voltage, which, in one embodiment, is 100 kVp (block 324). Decreasing the peak tube voltage typically results in an increase in contrast of the CT scan image, and the relationship between decreased tube voltage and increased contrast is known for the various types of CT scans. Reducing the voltage, however, also results in an increase in noise of the resulting image, the magnitude of which depends on the WED of the scanned area of the patient. The controller is configured to identify a percent increase in the noise level resulting from decreasing the voltage from the first voltage to the reduced voltage and from the WED of the scanned area (block 328).

Increasing the tube current is known to reduce noise level in the resulting scan, while decreasing the tube current increases noise level. The quality of the image generated during a scan is typically a function of the ratio of the image contrast to the image noise level, also known as the signal-to-noise ratio. As such, the controller 120 identifies a tube current that equates the overall percent increase in noise resulting from the reduced voltage and modified current with the increase in contrast resulting from reducing the tube voltage (block 332). Operating the CT scanner with the identified tube current and the reduced voltage therefore results in an image having the same relative increase in both contrast and noise, and thus the image has the same signal-to-noise ratio as an image produced at the first, higher, voltage. The reduction in voltage, however, results in a reduced radiation dose to the patient. The controller is configured to calculate the radiation dose output from the CT scan, also known as the "CT dose index" or "CTDI vol," corresponding to the reduced voltage and the identified current that retains a constant signal-to-noise ratio (block 336). The CTDI vol specifies the radiation intensity used to perform a specific CT examination and is the metric used by the American College of Radiology (ACR) for CT practice accreditation. The CTDI vol depends on many factors including the tube current, peak tube voltage, diameter and geometry of the gantry, and types of X-ray tube filters.

The process 300 continues by determining whether a corresponding tube current and CTDI vol need to be calculated for additional reduced voltages (block 340). In one embodiment, the CT scanner is configured to calculate a tube current and CTDI for reduced voltages of 100 kVp and 80 kVp, though in other embodiments, additional or alternate voltages can be selected. The process 300 continues from block 324 to identify tube current and CTDI for additional reduced voltages if any remain. After the additional reduced voltages have been evaluated, the controller 120 proceeds to operate the X-ray source 108 at the reduced voltage and corresponding current having the lowest identified radiation dose (block 344).

The process 300 therefore enables a reduction in CTDI from the first voltage by automatically selecting a tube current and peak voltage that does not reduce image quality with reference to the signal-to-noise ratio. Further, because the process is customized to a particular institution, radiologist, or department, the automated process is flexible enough to be used in a variety of different institutions or departments.

While the preferred embodiments have been illustrated and described in detail in the drawings and foregoing description, the same should be considered illustrative and not restrictive. While preferred embodiments have been presented, all changes, modifications, and further applications are desired to be protected.

What is claimed is:

1. A method of operating a CT scanner comprising:
receiving data associated with the CT scanner with a controller associated with the CT scanner, each datum of the data including a noise level and a water equivalent diameter for a patient imaged in a CT scan generated by the CT scanner that has an image quality above a predetermined image quality threshold;
storing with the controller the data in a memory associated with the CT scanner;
generating with the controller associated with the CT scanner a curve identifying acceptable noise levels with reference to the water equivalent diameters in the data;
storing with the controller the curve in the memory; and
operating with the controller the CT scanner to perform a subject scan with a current level and a voltage level for an X-ray tube in the CT scanner being selected with reference to the curve stored in the memory and a water equivalent diameter for a patient to be imaged.

2. The method of claim 1 the operating of the CT scanner further comprising:
operating with the controller the CT scanner to perform a first scan of a subject;

generating with the controller image data corresponding to the first scan;

identifying with the controller a first water equivalent diameter with reference to the image data; and selecting with the controller a first noise level with reference to the identified first water equivalent diameter and the curve stored in the memory.

3. The method of claim 2 the operating of the CT scanner further comprising:

identifying with the controller a first contrast level at a first voltage level of the X-ray tube;

identifying with the controller a percent increase in contrast from the first contrast level for at least a second voltage level and a third voltage level for the X-ray tube, the second and third voltage levels being less than the first voltage level;

identifying with the controller a current level of the X-ray tube with reference to the first water equivalent diameter and the first noise level, the current level the X-ray tube corresponding to a percent increase in noise from the first noise level that is equal to the percent increase in contrast for each of the at least second and third voltage levels;

identifying with the controller a radiation dose for each of the at least second and third voltage levels and the corresponding identified current level with reference to dosage data stored in the memory;

selecting with the controller a minimum radiation dose from the identified radiation doses that corresponds to one of the at least second and third voltage levels; and operating with the controller the CT scanner to perform the subject scan with the X-ray tube using the identified current level and corresponding one of the at least second and third voltage levels that corresponds to the selected minimum dose.

4. A CT scanner comprising:

an X-ray tube;

a plurality of X-ray detectors; and a controller operatively connected to the X-ray tube and the plurality of X-ray detectors, the controller being associated with a memory and being configured to:

receive data corresponding to images generated by the plurality of X-ray detectors, each datum of the data including a noise level and a water equivalent diameter for a patient imaged in a CT scan having an image quality above a predetermined image quality threshold;

store the data in the memory;

generate a curve identifying acceptable noise levels with reference to the water equivalent diameters in the data;

store the curve in the memory; and operate the X-ray tube to perform a subject scan with a current level and a voltage level for the X-ray tube being selected with reference to the curve stored in the memory and a water equivalent diameter for a patient to be imaged.

5. A CT scanner of claim 4 the controller being further configured to:

operate the X-ray tube and the X-ray detectors to perform a first scan of a subject;

generate image data corresponding to data received from the plurality of X-ray detectors during the first scan;

identify a first water equivalent diameter with reference to the image data; and select a first noise level with reference to the identified first water equivalent diameter and the curve stored in the memory.

6. The CT scanner of claim 5, the controller being further configured to:

identify a first contrast level at a first voltage level for the X-ray tube;

identify a percent increase in contrast from the first contrast level for at least a second and a third voltage level for the X-ray tube, the second and third voltage levels being less than the first voltage level;

identify with reference to the first water equivalent diameter and the first noise level, the current level of the X-ray tube corresponding to a percent increase in noise from the first noise level that is equal to the percent increase in contrast for each of the at least second and third voltage levels;

identify a radiation dose for each of the at least second and third voltage levels and the corresponding identified current level for the X-ray tube with reference to dosage data stored in the memory;

select a minimum radiation dose from the identified radiation doses that corresponds to one of the at least second and third voltage levels; and operate the X-ray tube to perform the subject scan using the identified current level and the corresponding one of the at least second and third voltages that corresponds to the selected minimum dose.

* * * * *